US00PP14700P29

(12) United States Plant Patent
Bell

(10) Patent No.: US PP14,700 P2
(45) Date of Patent: Apr. 13, 2004

(54) SHRUB ROSE PLANT NAMED 'RADYOD'

(50) Latin Name: *Rosa hybrida*
Varietal Denomination: Radyod

(75) Inventor: John M. Bell, Lancaster, PA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 10/336,811

(22) Filed: Jan. 6, 2003

(51) Int. Cl.[7] ..... A01H 5/00
(52) U.S. Cl. ..... Plt./102
(58) Field of Search ..... Plt./102

*Primary Examiner*—Bruce R. Campell
*Assistant Examiner*—Annette H Para
(74) *Attorney, Agent, or Firm*—Burns, Doane, Swecker & Mathis, L.L.P.

(57) ABSTRACT

A new and distinct variety of landscape shrub rose plant is provided which forms in abundance on a substantially continuous basis attractive single blossoms that are light pink in coloration. The new variety is a spontaneous mutation of unknown causation of the 'Radrazz' variety (U.S. Plant Pat. No. 11,836) that forms vivid red single blossoms. The vegetation is vigorous and the growth habit is compact, spreading, and mounding. Attractive ornamental glaucous medium green to bluish-green foliage is formed. Excellent disease resistance to blackspot is exhibited. The new variety is particularly well suited for growing as distinctive ornamentation in the landscape.

11 Drawing Sheets

Botanical/commercial classification: *Rosa hybrida*/Shrub Rose Plant.
Varietal denomination: cv. 'Radyod'.

SUMMARY OF THE INVENTION

The new variety of *Rosa hybrida* landscape shrub rose plant of the present invention was discovered during June, 2001 while growing among a block of rose plants of the 'Radrazz' variety (U.S. Plant Pat. No. 11,836) present in a nursery setting at Blairsville, Pa., U.S.A. I was attracted to the new variety primarily because of its distinctive light pink blossom coloration and foliage coloration that was unlike that of the parental variety. Such blossoms were found to mature to an even lighter pink that approaches a light blush pink or apple-blossom coloration when exposed to increasing temperatures. At higher temperatures the very pale pink blossoms may even assume a near white coloration at full maturity. The new variety is believed to be a spontaneous naturally-occurring mutation of the 'Radrazz' variety of unknown causation. Had I not discovered and preserved the original plant of the new variety it would have been lost to mankind.

It was found that the new variety of landscape shrub rose plant of the present invention possesses the following combination of characteristics:

(a) abundantly and substantially continuously forms attractive single blossoms that are light pink in coloration unlike the vivid red blossoms of the 'Radrazz' variety (U.S. Plant Pat. No. 11,836), (b) exhibits a compact, spreading, and mounding growth habit, (c) forms vigorous vegetation, (d) forms attractive ornamental glaucous medium green to bluish-green foliage, and (e) exhibits excellent resistance to blackspot.

The new rose variety has attractive light pink blooms, combined with a propensity for everblooming and blackspot resistance. The blooming cycle corresponds closely to that of the 'Radrazz' parental variety.

The new variety of the present invention can be readily distinguished from the parental 'Radrazz' variety and the 'Radcon' variety (U.S. Plant patent application Ser. No. 10/335,865, filed Jan. 3, 2003) through an inspection of the blossoms. More specifically, the new variety displays single blossoms that are light pink in coloration rather than vivid red blossoms as are displayed by the 'Radrazz' variety, and the darker pink blossoms of the 'Radcon' variety.

The new variety well meets the needs of the horticultural industry. It can be grown to advantage as attractive ornamentation in parks, gardens, public areas, and residential landscapes. Accordingly, it is particularly well suited for growing throughout the landscape. The light pink blossoms contrast nicely with the glaucous medium green to bluish-green foliage.

The characteristics of the new variety have been found at West Grove, Pa., U.S.A., and at Wasco, Calif., U.S.A., to be homogeneous and stable and are strictly transmissible by asexual propagation such as budding, grafting, and the use of cuttings from one generation to another.

The new variety has been named the 'Radyod' variety. The new 'Radyod' variety is being marketed under the BLUSHING KNOCK OUT trademark.

BRIEF DESCRIPTION OF THE PHOTOGRAPHS

The accompanying photographs show, as nearly true as it is reasonably possible to make the same in a color illustrations of this character, typical specimens of the new variety. The rose plants were approximately two years of age and were grown in the ground outdoors on their own roots during July, August, and September at West Grove, Pa., U.S.A. Dimensions in centimeters are included at the bottom of each photograph except FIG. 13.

DETAILED DESCRIPTION

Figure 1:
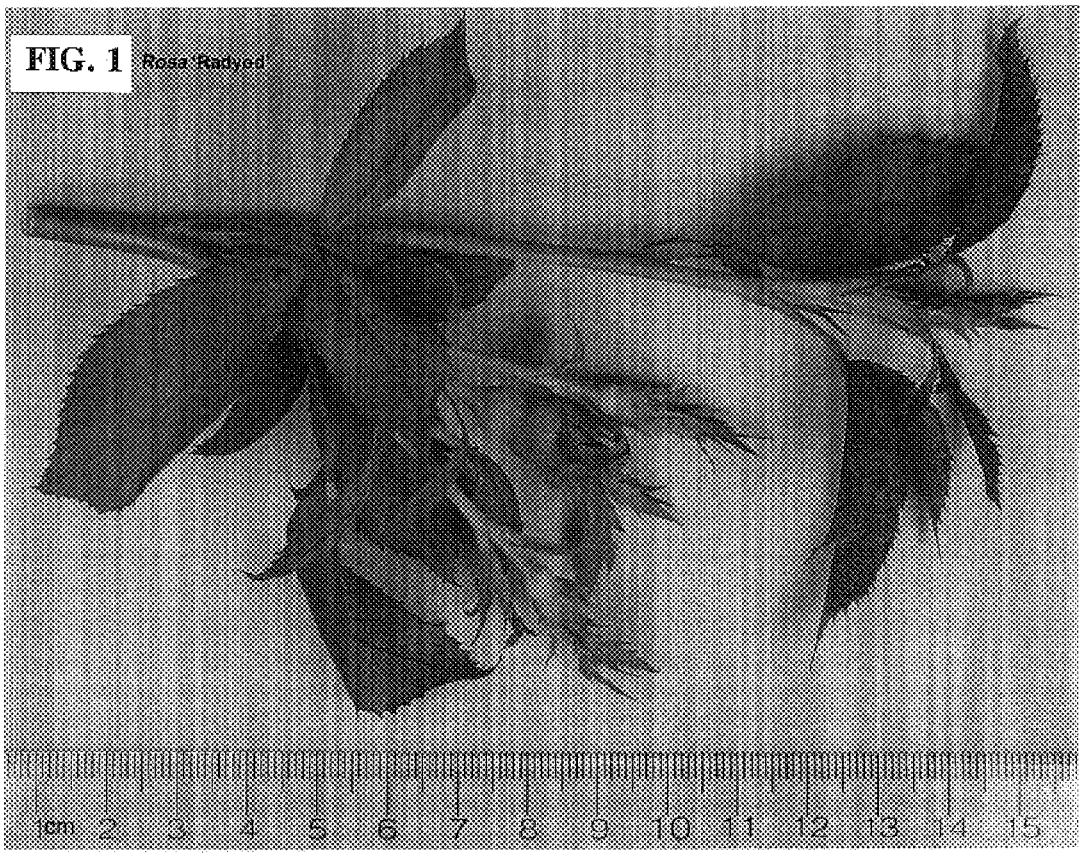
FIG. 1 illustrates a specimen of a typical young flowering shoot of the new variety.
Figures 2, 3, 4:
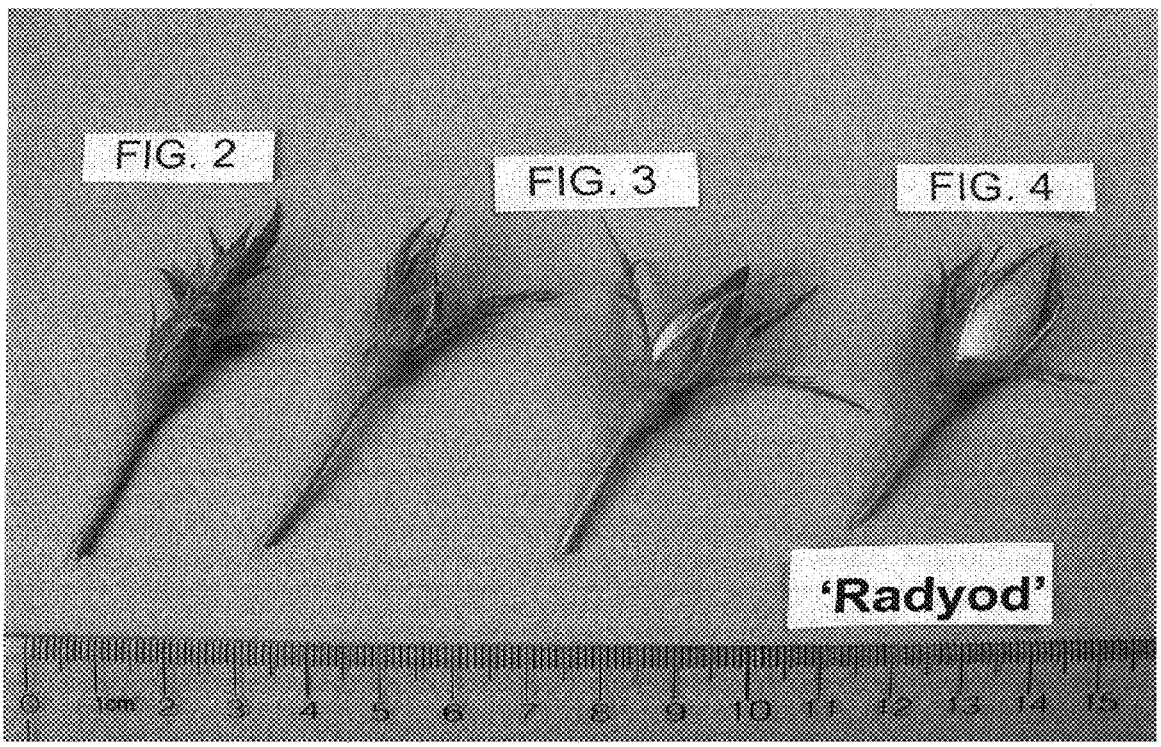
FIG. 2 illustrates a specimen of typical floral bud of the new variety before the opening of the sepals.
FIG. 3 illustrates specimens of two floral buds of the new variety at progressing stages of the opening of the sepals.
FIG. 4 illustrates a specimen of a floral bud of the new variety as the petals begin to open.

The chart used in the identification of colors is that of The Royal Horticultural Society (R.H.S. Colour Chart). The description is based on the observation of approximately two year-old specimens of the new variety during July, August, and September while grown in the ground outdoors on their own roots at West Grove, Pa., U.S.A.

Class: Landscape Shrub Rose.

Plant:

*Height.*—Aproximatdy 50 to 75 cm on average at the end of the growing season.

*Width.*—Approximately 75 to 100 cm on average at the end of the growing season.

*Habit.*—Compact, spreading, and mounding.

Branches:

*Color.*—Young flowering stems: slightly glaucous, and the coloration commonly is near and through Yellow-Green Group 144A, 146B, and 146C.

*Prickles.*—Size: approximately 0.9 to 1.6 cm in length and approximately 0.7 to 1.2 cm in width at the base parallel to stem axis. The larger prickles typically are found towards the base on the more vigorously growing stems that become flowering shoots. Shape: the upper edge tends to be more or less straight and to point downwards at an angle of approximately 20 to 40 degrees below the horizontal, and the lower edge commonly is convex when viewed from above. The base configuration is slightly obovate, and narrowing towards the base of the stem. Frequency: on the lower portion of a flowering stem approximately 9 to 12 prickles over a span of 15 cm, and on the upper portion of a flowering stem there commonly are very few prickles of any size. Color: variable with a base color near Green Group 138B, 138C, and 139C, and to a lesser extent near Greyed-Green Group 193A. Some purplish coloration in the greatest concentration at the base is Greyed-Purple Group 185A, 185B, 186A, 187B and 187C. These purplish tones tend to appear as a wash of color.

Leaves:

*Leaflets.*—Number: 3, 5, and 7. Typically leaves having 3 and 5 leaflets are more common. Arrangement: alternate and odd-pinnately compound. Shape: narrowly elliptical to elliptical to slightly ovate with a serrate to serrulate margin that commonly is slightly to occasionally strongly revolute, broadly rounded to broadly cuneate to inequilaterus or strongly oblique base, broadly acuminate to abruptly acuminate tip, and commonly with distinct concave cupping. The distinct rolling of the margin and cupping of the leaflets is a distinguishing characteristic of the variety. Overall leaf size: commonly approximately 5 to 16 cm in length, and approximately 5 to 15 cm in width. The 3-leaflet leaves are found most commonly in the lower one-half of the ranges, and the 5- and 7-leaflet leaves are found most commonly in the upper one-half of the ranges. The overall leaflet size has been found to vary greatly. Leaves measuring outside the specified ranges sometimes appear with their size being influenced by the time within the growing season, the plant vigor being displayed, their location on the stem, and the environmental and cultural conditions being experienced. Leaflet size: the terminal leaflets typically are approximately 5.5 to 8.5 cm in length and approximately 2.5 to 4.5 cm in width. Most commonly the length is approximately 6.5 to 7.5 cm and the width is approximately 3 to 4 cm. Serration: fine. Texture: glabrous with a slight glaucous coating. Overall appearance: very dense, leathery, and medium green with a bluish cast in coloration, and with a matte finish on the ventral surface. Color (young leaflets): both surfaces are near Greyed-Purple Group 187A and 187B over a green base coloration. The venation is near Greyed-Purple Group 187A and 187B, and Red-Purple Group 59A. The margin of a developing leaflet commonly retains much of such coloration and is near Greyed-Purple Group 185A, 187A and 187B, and Red-Purple Group 59A. Color (mature leaflets): Upper surface: near Green Group 137A on lighter foliage and near Green Group 139A on darker foliage. Under surface: near Greyed-Green Group 191A and becoming near Green Group 137C when a glaucous coating is removed. The veins on the under surface are near Yellow-Green Group 146C.

*Petioles.*—Length: typically approximately 1.3 to 2.5 cm, and most commonly approximately 1.7 to 2.0 cm. Diameter: typically approximately 1.3 to 2.2 mm, and most commonly approximately 1.3 to 1.5 mm. Color (upper surface): near Green Group 137B and 138A. Color (lower surface): near Yellow-Green Group 144A, 146B and 146C. Texture: stiff glandular hairs are present on both surfaces and tend to be more common on the upper surface. These stiff glandular hairs typically range from approximately 0.1 to 0.5 mm in length. A few minute reddish prickles are scattered on the lower surface that are near Greyed-Purple Group 186A, 186B, 187A and 187B in coloration. The prickles typically are approximately 0.5 to 1.7 mm in length and most commonly are approximately 0.8 to 1.2 mm in length. Each petiole commonly bears approximately one or two prickles; however, up to about 5 prickles sometimes have been observed.

*Petiolules.*—The upper and lower surfaces commonly are near Red-Purple Group 187A in coloration.

*Rachis.*—Length: typically approximately 1.0 to 2.8 cm, and most commonly approximately 1.8 to 2.0 cm. Diameter: typically approximately 1.1 to 2.2 mm, and most commonly approximately 1.3 to 1.6 mm. Color (upper surface): when mature near Yellow-Green Group 146B with slightly lighter coloration near Green Group 137C and Yellow-Green Group 146C. Color (lower surface): when mature near Green Group 143C and Yellow-Green Group 146C. Texture: substantially the same as that of the petiole.

*Stipules.*—Configuration: revolute with two prominent reflexed horns and an elliptical body. Length: approximately 1.3 to 2.9 cm (average approximately 1.9 cm) from the tip of the base to the tip of the longest horn. Width: approximately 0.4 to 1.3 cm (average approximately 0.8 cm) across the tips of the horns, and approximately 0.3 to 0.8 cm (average approximately 0.6 cm) at the widest portion of the body. Color young stipule wings: near Greyed-Purple Group 185A, 185B, and 186A on the upper surface, and near Greyed-Purple Group 186A on the under surface. Color mature stipule wings: near Green Group 137A, 137B, 137C, and 138A on the upper surface, and near Green Group 137B, 137C, 138D and 138C on the under surface. Margin: serrulate to denticulate with each tooth commonly being terminated with a reddish somewhat stiff and hardened tip. Texture: young stipule wings tend to be glaucous, and when mature short reddish glandular hairs having lengths of approximately 0.1 to 0.2 mm that are near Greyed-Purple Group 187A and 187B in coloration at the tips commonly are present at the margin and near the petiole.

Inflorescence:

*Number of flowers.*—Occasionally solitary and commonly approximately 2 to 3 blooms per cluster on average and sometimes up to 5 or more in a cluster. As many as 40 blooms have been observed on a vigorous flowering stem during some observations.

*Buds.*—Shape: ovoid and small. Length: commonly approximately 1.2 to 1.5 cm. Diameter: commonly approximately 0.8 to 1.0 cm. Color (at bud crack): near Red-Purple Group 63B with darker areas near Greyed-Purple Group 185D and 186B. Color (during further opening): rapidly lightens and changes to near and through Red-Purple Group 73A, Red-Purple Group 62A, 62B, 62C, 65A, 65B, 65C, and 73C.

Figure 8:
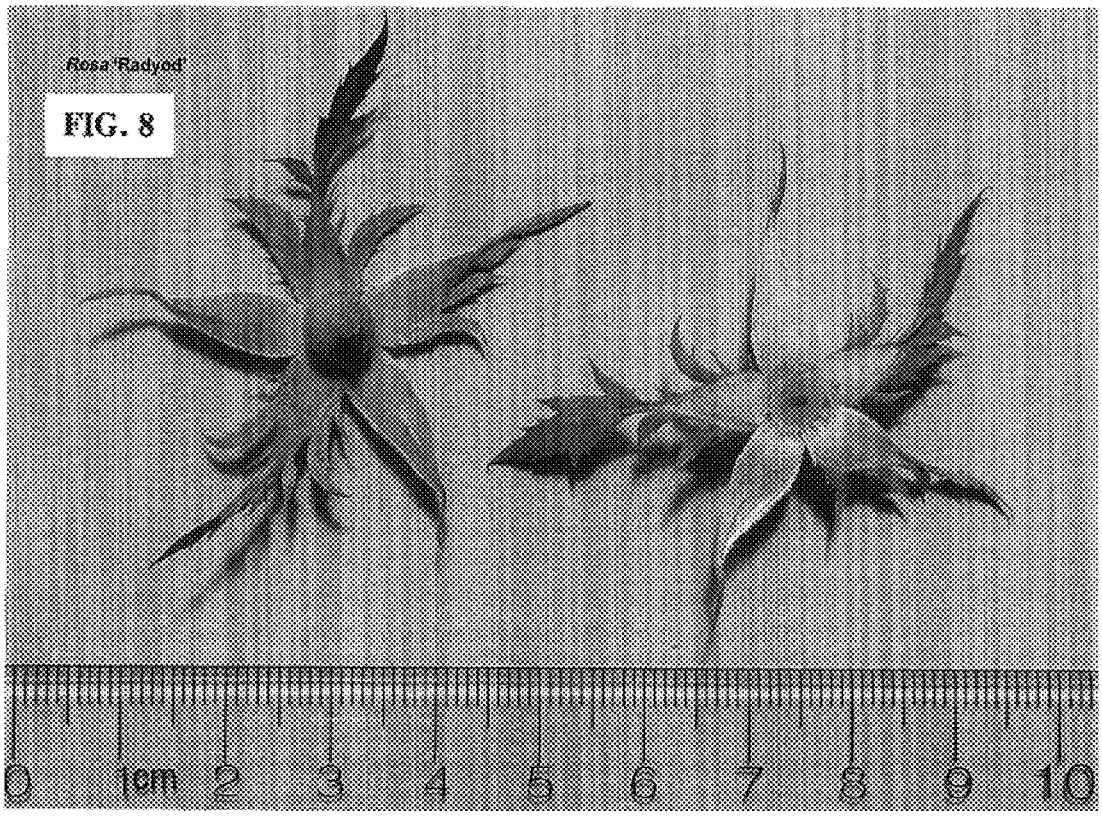
FIG. 8 illustrates specimens of typical sepals—plan view of obverse (right) and—plan view of reverse (left).
Figure 9:
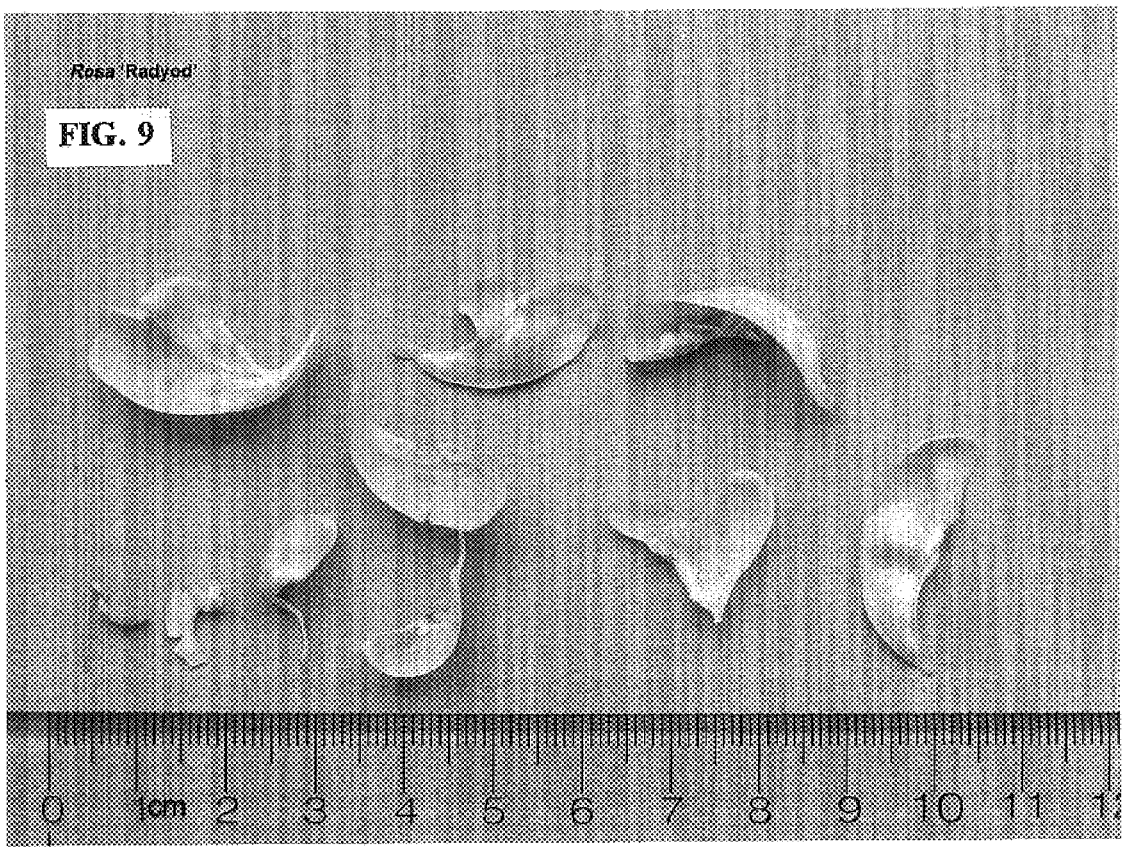
FIG. 9 illustrates specimens of typical petaloids showing various sizes and shapes.
Figure 10:
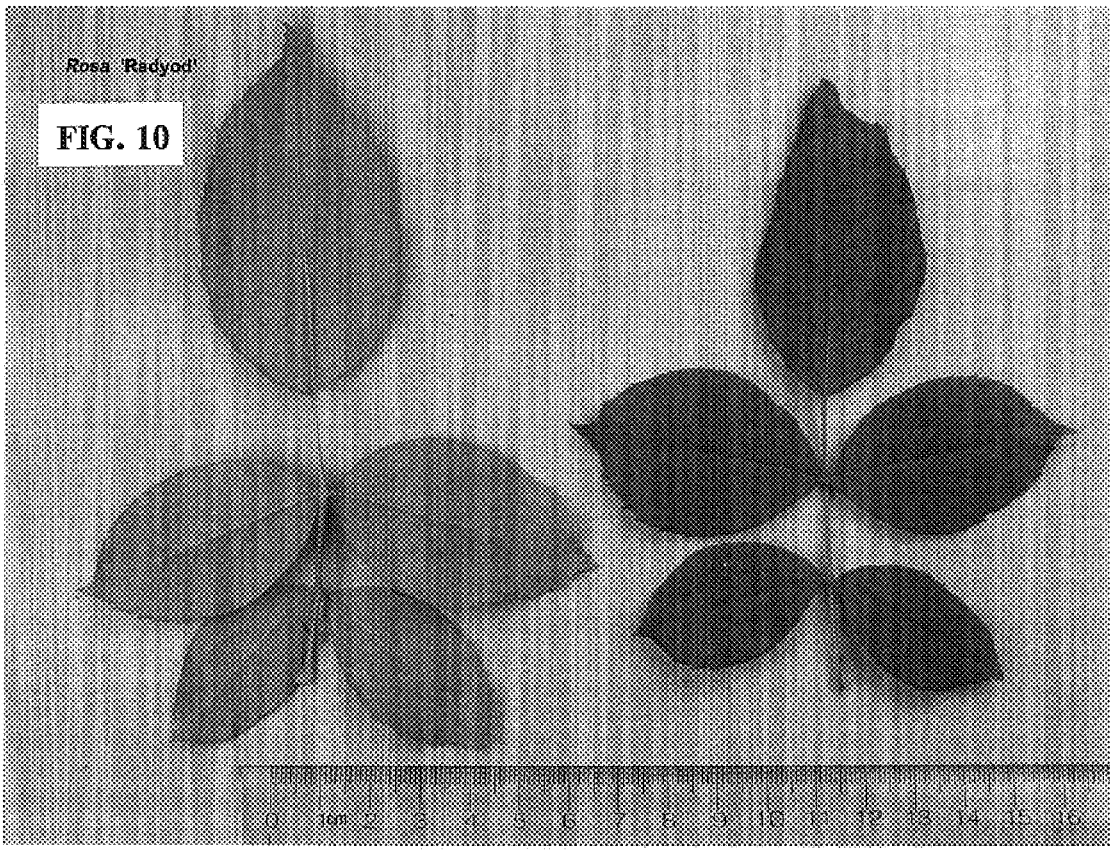
FIG. 10 illustrates specimens of leaves with five leaflets—plan view—upper surface (right) and under surface (left).
Figure 11:
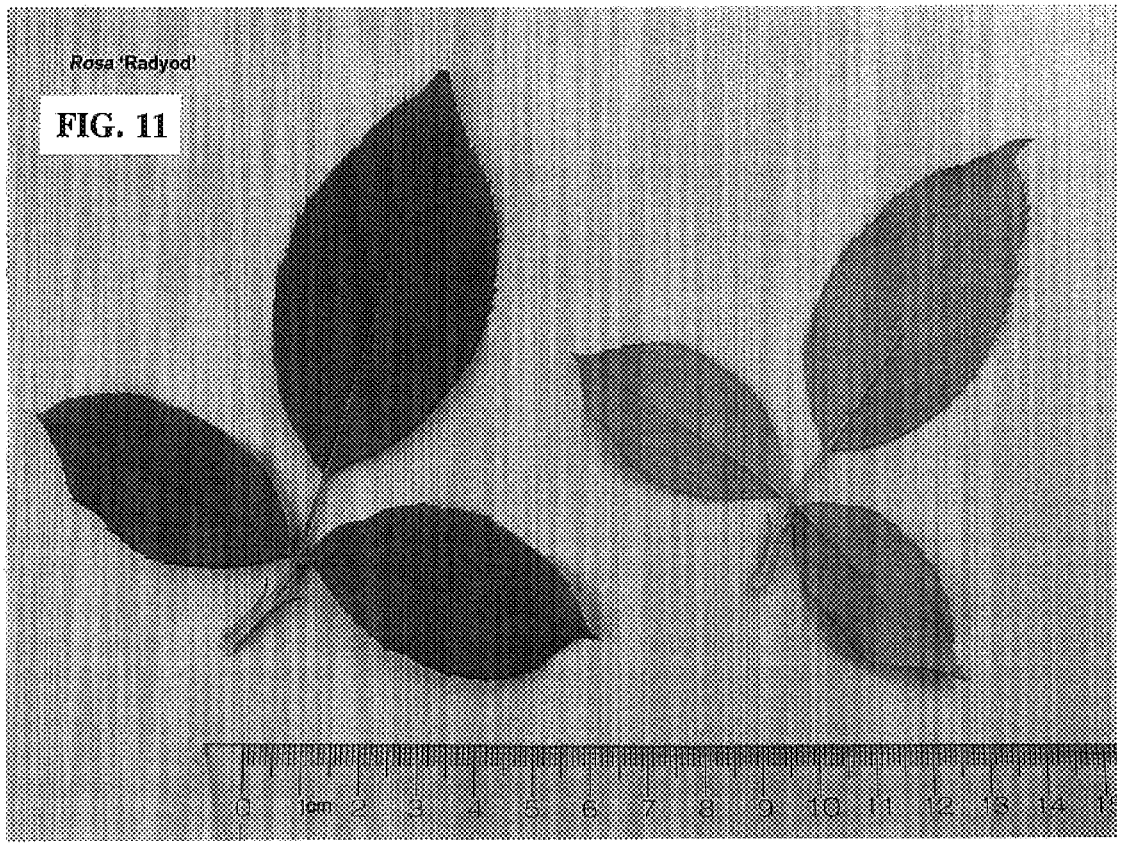
FIG. 11 illustrates specimens of leaves with three leaflets—plan view—upper surface (left) and under surface (right).
Figure 12:
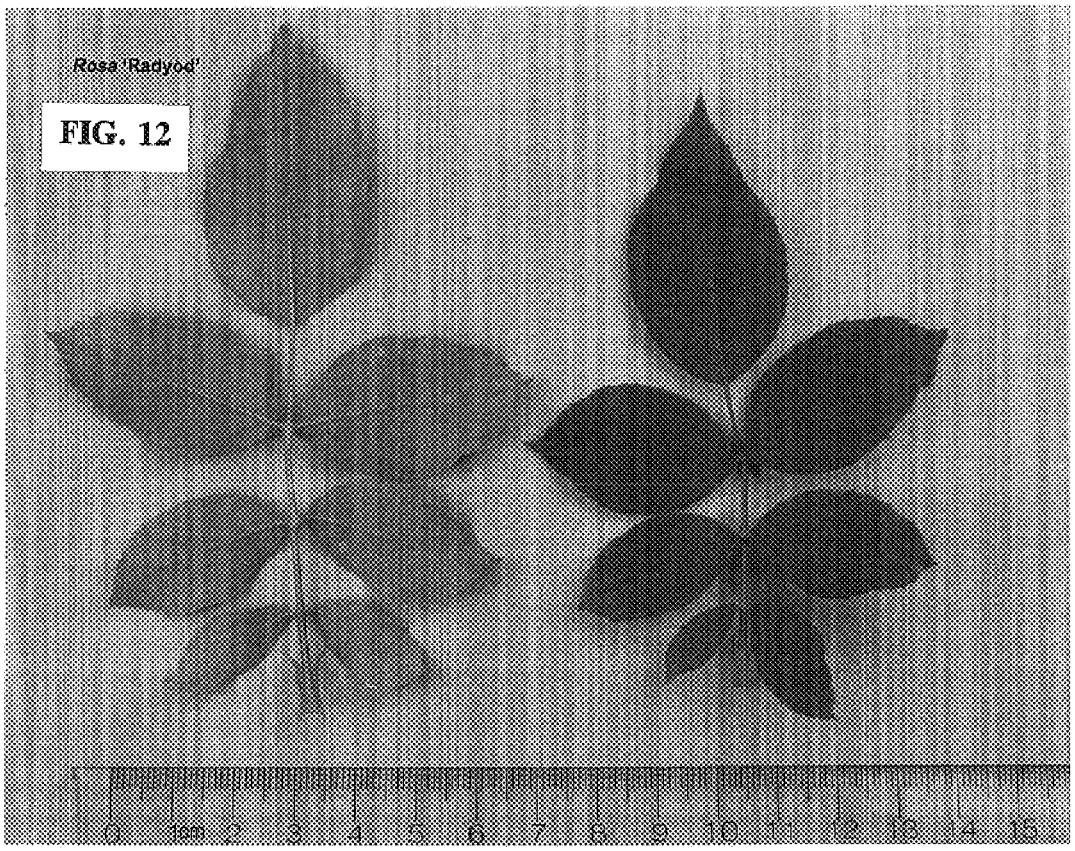
FIG. 12 illustrates specimens of leaves with seven leaflets—plan view—upper surface (right) and under surface (left).
Figure 13:
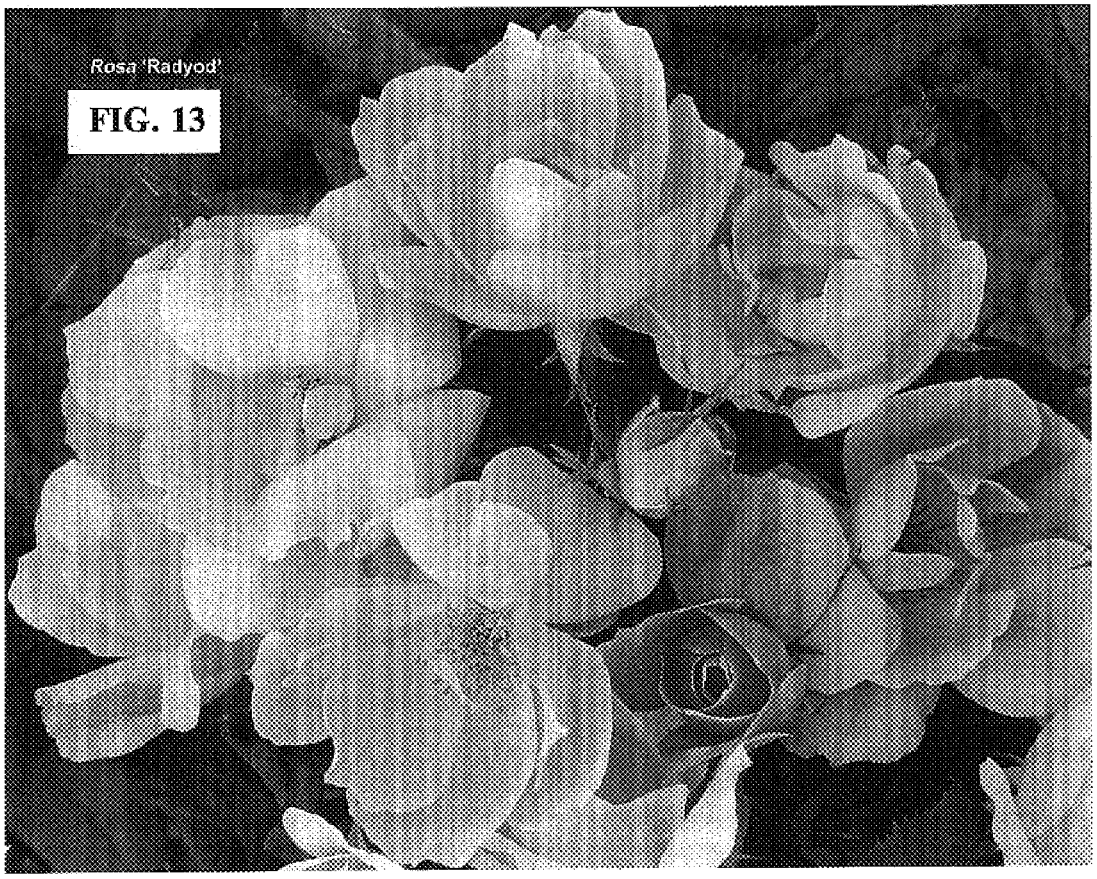
FIG. 13 illustrates a cluster of flowers at various stages of maturity.
Figure 14:
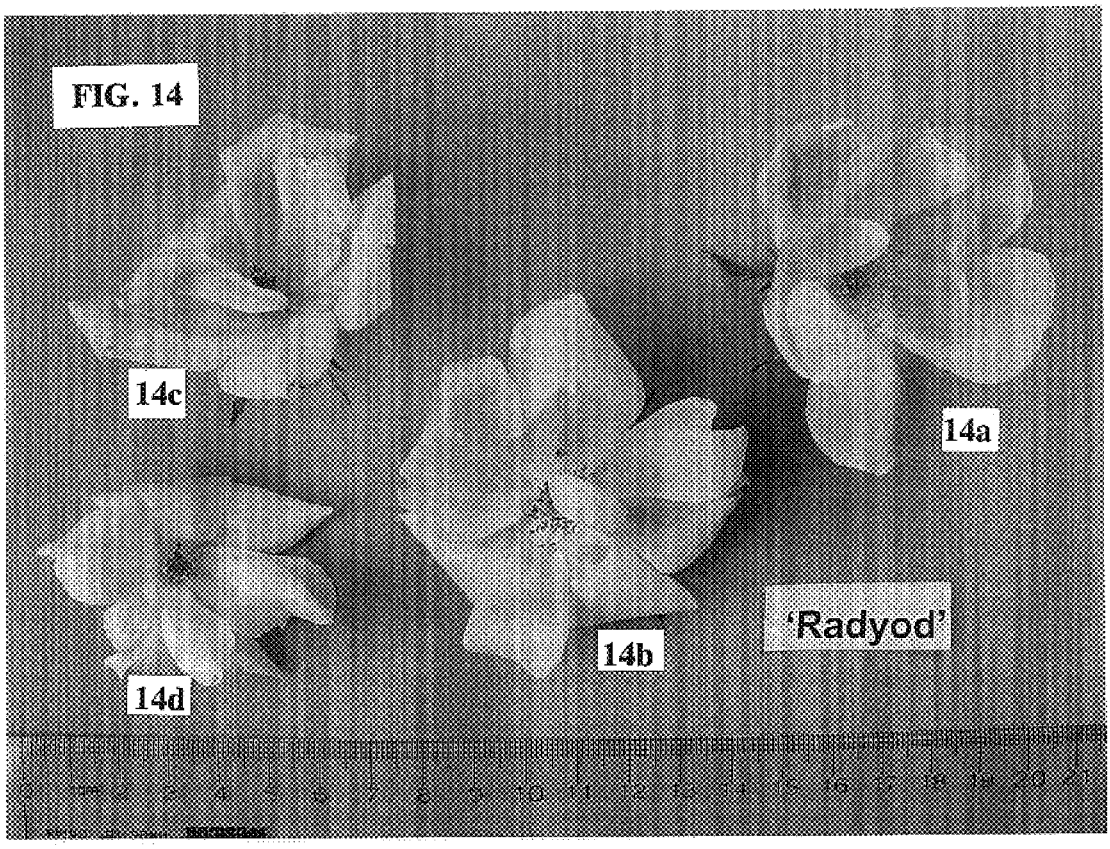
FIG. 14 illustrates specimens of typical flowers at various stages of maturity when grown under high temperature conditions with the youngest flowering being designated 14a and the oldest flower 14b.

*Flower.*—Form: single and informal. Diameter: variable depending upon the time of the year and the vigor of the plant. A diameter of approximately 5 to 7 cm commonly is displayed during mid-summer. Color (when blooming): The coloration is sensitive to heat and light levels which tend to lighten the color. During cooler seasons the blossoms are medium-light pink. Flowers that develop during the hotter months display coloration that is lighter pink and fade to near apple blossom white. Inner side of petals: the distal portions are near Red-Purple Group 62A, 62B, 62C, 62D, and 65A to near White Group 155D, and towards the base the coloration is Yellow Group 4B and 4C. The inner petals may also display darker areas of Red-Purple Group 68A, 68B, 73A, 73B, and 73C. In some instances the darker areas appear as thin lines. The veins impart no different coloration and are essentially colorless. Outer side of petals: in a fully open flower the coloration is substantially the same as on the inner side. Red-Purple Group 73C predominates towards the tip with occasional darker areas of Red-Purple Group 73A and 73B. This coloration lightens with maturity to Red-Purple Group 62C and 62D to near White Group 155D, and at the base the coloration is near Yellow Group 4C and 4D. Occasional spots and darker areas near Red-Purple Group 68A and 68B are present. Fragrance: light. Petal form: narrowly to broadly obovate. Petal base: narrowly cuneate to cuneate to narrowly rounded to rounded. Petal apex: broadly obtuse to rounded to truncate and rarely broadly acute. Commonly is softly apiculate to occasionally slightly emarginated and occasionally slightly praemorsus. Petal margin: mostly entire, and occasionally becoming slightly undulate towards the apex. The petals tend to become revolute towards the apex as the flower matures. Petal number: approximately 5 to 11, and most commonly 7 to 9 on average. Petaloid number: commonly 0 to approximately 5, with an average of approximately 2 per flower. Petaloid shape: highly variable, and most commonly falcate. Petaloid length: commonly approximately 8 to 29 mm measured across the arc. Petaloid width: commonly approximately 3 to 19 mm at the widest point. Petaloid texture: typically opaque, glabrous, and soft. Petaloid color (both sides): near Red-Purple Group 62A, 62B, 62C and 62D towards the distal end with Red-Purple Group 62B and 62C being predominant, and towards the base near Red Group 49D to White Group 155B, 155C and 155D, and near Yellow Group 4C at the very base. Some petaloids show areas of Red-Purple Group 68A and 68B that appear as scattered darker areas that typically are present on the inner surface and towards the edges. Stamen number: commonly approximately 120 on average. Filament length: variable, and commonly approximately 2 to 10 mm. Filament color: Yellow-Orange Group 20A near the base, and towards the anther Yellow-Orange Group 20B, and Yellow Group 13B and 13C immediately adjacent the anther. Anther size: immediately prior to and during anthesis approximately 1.2 to 2.0 mm in length. Anther color: when flowers first open near Greyed-Yellow Group 160A and 160B, changing with maturity to near Greyed-Orange Group 163C. Pistil number: commonly approximately 32 to 40 with an average of approximately 37. Style length: commonly approximately 8 to 11 mm with an average of approximately 9 mm, and commonly are kinked at a few locations. Style color: near Greyed-Purple Group 185C through Red-Purple Group 60B and 60C and Greyed-Purple Group 185B approaching Greyed-Purple Group 185A with the lightest coloration being present at the base. Stigma size: commonly approximately 0.5 to 0.9 mm in diameter with an average diameter of approximately 0.7 mm. Stigma color: near Greyed-Yellow Group 162A. Pollen: it appears that viable pollen is formed in a sparse quantity with no active discharge commonly being observed in flowers. When the anther is crushed some yellow-orange pollen has been observed. Receptacle length: commonly approximately 7.5 to 9.5 mm, and approximately 8.5 mm on average. Receptacle width: commonly approximately 6.2 to 7.5 mm, and approximately 7.5 mm on average. Receptacle texture: glaucous with a waxy coating. Commonly smooth over approximately 75 percent of the surface, with the lower approximately 25 percent of the surface bearing scattered minute stiff reddish glandular hairs, and occasional prickles that are more common on the lower approximately 10 to 15 percent of the surface. The hairs and prickles commonly range in length from approximately 0.1 to 1 mm and are near Greyed-Purple Group 187B in coloration. Receptacle color: the base color is near Green Group 143A and 143B. Lasting quality: commonly approximately 1½ to 2 weeks on the plant. The vase life appears to be variable with blossoms sometimes lasting up to 10 days. Petal drop: very good with the petals commonly dropping cleanly and freely. However, under prolonged rainy growing conditions the petals may persist somewhat. Sepal number: 5. Sepal length: commonly approximately 18 to 27 mm, with an average of length of approximately 22 mm. Sepal width: commonly approximately 4 to 7 mm at the widest point with an average width of approximately 5.5 mm. Sepal extensions: commonly present and feathery foliaceous. See FIG. 8 for an illustration of representative sepals. The frequency of the extensions commonly ranges from zero to 6 or more plus an expanded feathery tip. Typically the shortest sepal will have no foliaceous extensions, the next shortest sepal will have none or occasionally 1 and rarely 2 foliaceous extensions, the third shortest sepal will have 2 to 3 and occasionally 4 foliaceous extensions, and the two longest sepals will have 4 or 5 and occasionally 6 foliaceous extensions plus have the longest and most feathered tips. Sepal apex: commonly narrowly acuminate to acuminate when lacking a foliaceous extension. Sepal base: commonly fused at the base to the receptacle and to adjoining sepals, hence there is no distinct base shape. Overall sepal shape: substantially lanceolate. Sepal texture: the inner surface is moderately densely covered with silvery-white lanate hairs giving an effective color of near White Group 155C with a light greenish hue to the hairs overlaying the green base tissue. Small reddish-tipped glandular hairs typically are present on inner surfaces at the margins and marginal areas and are rarely present in the medial are. These hairs commonly are approximately 0.1 to 0.5 mm in length and are more common on those sepals that bear foliaceous extensions. The same glandular hairs are commonly sparsely scattered across the outer surfaces of the sepals, and are more common on the outer surfaces of those sepals bearing foliaceous extensions. Sepal color: darker at the tip and lighter at the base, near Green Group 137C, 143A, 143B and Yellow-Green Group 144A, and 144B. On the outer surface the foliaceous extensions commonly are somewhat transparent and appear to be near Greyed-Purple Group 187B with green showing through.

Development:

*Vegetation.*—Vigorous and strong.

*Blossoming.*—Abundant and substantially continuous.

*Resistance to diseases.*—Excellent with respect to rose blackspot.

*Propensity to form hips.*—None observed to date under greenhouse growing conditions. When grown outdoors, a small quantity of fruit has set; however, it is not known whether such fruit is viable.

The new 'Radyod' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of landscape shrub rose plant characterized by the following combination of characteristics:

(a) abundantly and substantially continuously forms attractive single blossoms that are light pink in coloration unlike the vivid red blossoms of the 'Radrazz' variety (U.S. Plant Pat. No. 11,836), (b) exhibits a compact, spreading, and mounding growth habit, (c) forms vigorous vegetation, (d) forms attractive ornamental glaucous medium green to bluish-green foliage, and (e) exhibits excellent resistance to blackspot;

substantially as herein shown and described.

* * * * *

FIG. 1 Rosa 'Radyed'

'Radyod'

Figure 5:
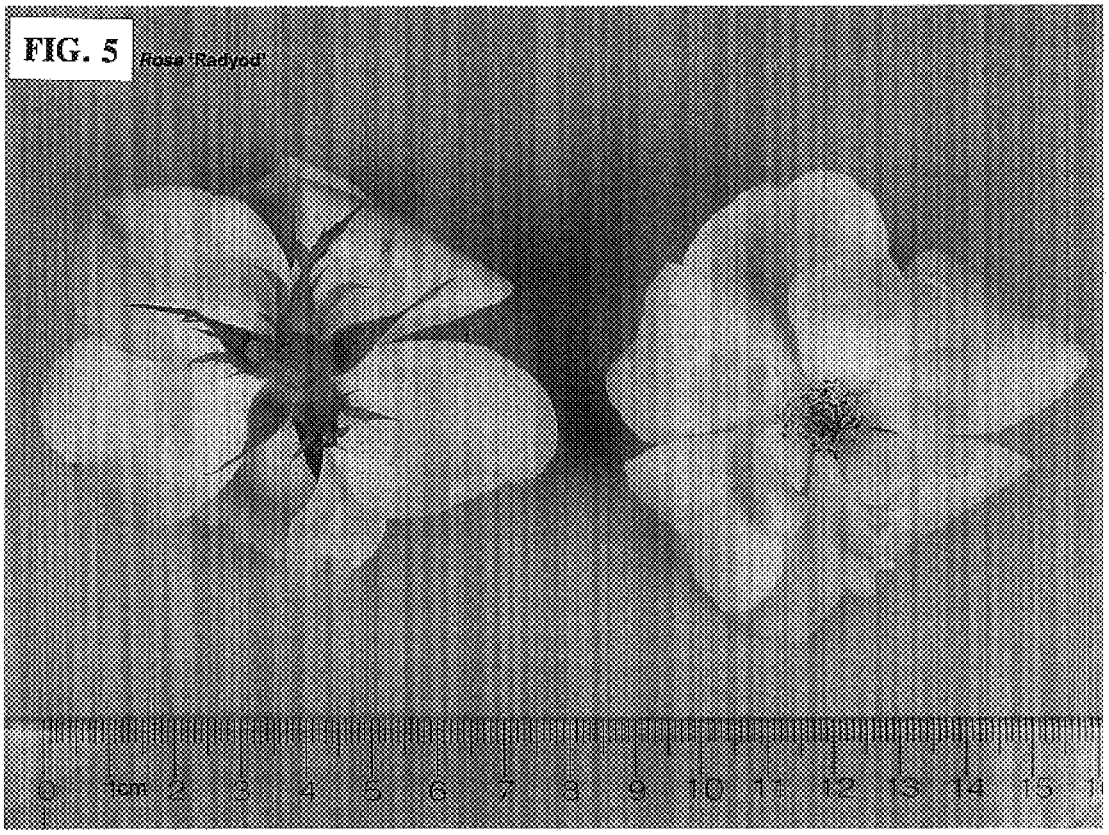
FIG. 5 illustrates the fully open light pink flowers of the new variety with the obverse view being presented on the right and the reverse view being presented on the left.
Figures 6, 7:
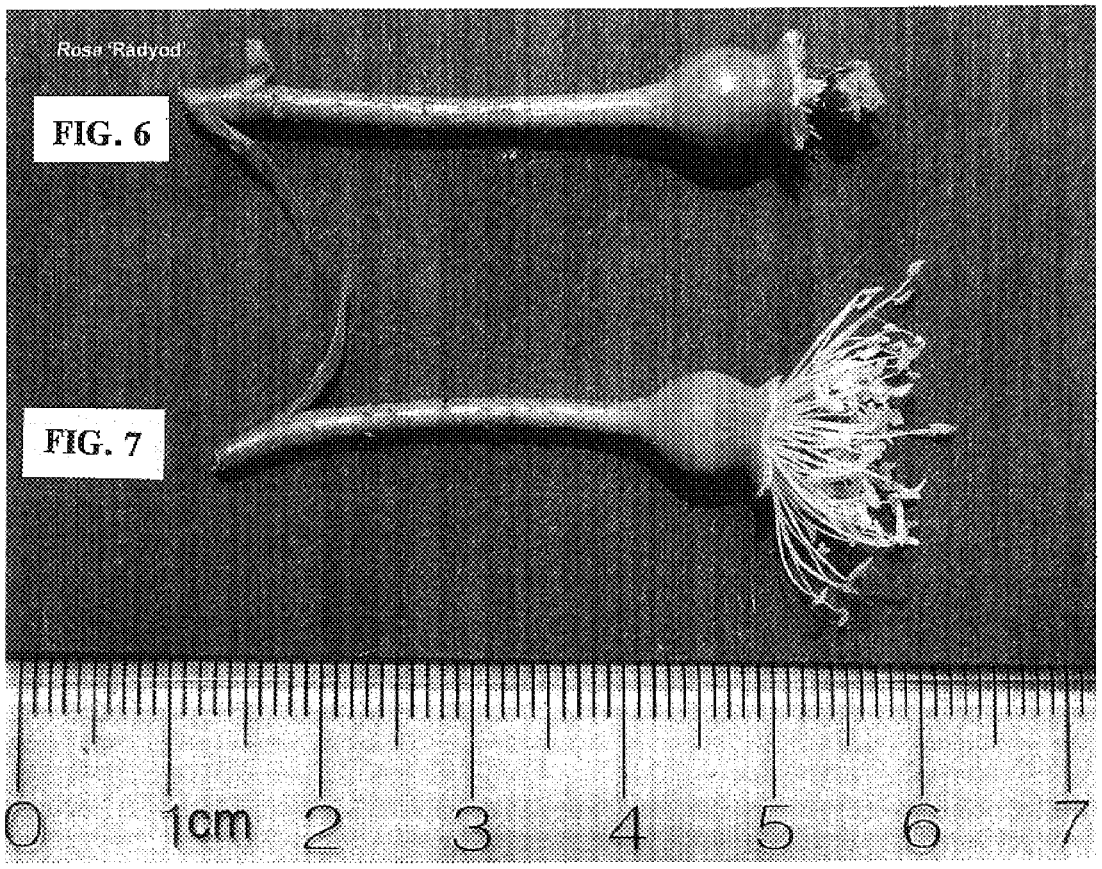
FIG. 6 illustrates a specimen of a floral receptacle showing the arrangement of the pistils (stamens removed).
FIG. 7 illustrates a specimen of a floral receptacle showing the arrangement of the pistils and stamens.

FIG. 5 *Rosa* 'Radyrod'

Rosa 'Radyod'

0 1cm 2 3 4 5 6 7 8 9 10 11 12 13 14 15

14c
14a
'Radyod'
14b
14d